(12) United States Patent
Robertson

(10) Patent No.: US 8,187,659 B2
(45) Date of Patent: May 29, 2012

(54) SOLID MEDICAMENT DOSAGE FORM CONSUMPTION AID

(75) Inventor: Jerry Robertson, Corcoran, CA (US)

(73) Assignee: Jerry Robertson Real Estate LLC, Corcoran, CA (US)

( * ) Notice: Subject to any disclaimer, the term of this patent is extended or adjusted under 35 U.S.C. 154(b) by 463 days.

(21) Appl. No.: 11/381,281

(22) Filed: May 2, 2006

(65) Prior Publication Data

US 2007/0259038 A1  Nov. 8, 2007

(51) Int. Cl.
*A61K 9/28* (2006.01)
(52) U.S. Cl. ............ 427/2.14; 118/300; 106/162.1
(58) Field of Classification Search ........... 427/2.14; 118/300; 106/162.1
See application file for complete search history.

(56) References Cited

U.S. PATENT DOCUMENTS

| | | | |
|---|---|---|---|
| 2,436,505 A | 2/1948 | Du Rall | |
| 3,316,150 A | 4/1967 | Faeges | |
| 4,123,532 A | 10/1978 | Vogt | |
| 4,145,440 A * | 3/1979 | Fitch et al. | 514/570 |
| 4,284,649 A | 8/1981 | Wiczer | |
| 4,581,013 A | 4/1986 | Allen | |
| 4,760,096 A | 7/1988 | Sakai et al. | |
| 4,792,333 A | 12/1988 | Kidder | |
| 4,863,741 A | 9/1989 | Becker | |
| 5,206,030 A | 4/1993 | Wheatley et al. | |
| 5,464,631 A | 11/1995 | Hoover et al. | |
| 5,605,889 A | 2/1997 | Curatolo et al. | |
| 5,643,204 A | 7/1997 | Cover | |
| 5,670,168 A | 9/1997 | Baichwal et al. | |
| 5,683,717 A | 11/1997 | Shen | |
| 6,083,489 A * | 7/2000 | Fischer et al. | 424/52 |
| 6,143,276 A | 11/2000 | Unger | |
| 6,183,808 B1 * | 2/2001 | Grillo et al. | 427/2.14 |
| 6,274,162 B1 | 8/2001 | Steffenino et al. | |
| 6,277,395 B1 * | 8/2001 | Fukui et al. | 424/439 |
| 6,326,028 B1 * | 12/2001 | Nivaggioli et al. | 424/481 |
| 6,337,083 B1 | 1/2002 | Fuisz | |
| 6,471,992 B1 | 10/2002 | Yoo et al. | |
| 7,118,688 B2 | 10/2006 | Mora-Gutierrez et al. | |
| 2004/0115137 A1 * | 6/2004 | Verrall et al. | 424/48 |
| 2004/0234648 A1 * | 11/2004 | Mazurek et al. | 426/3 |
| 2004/0253276 A1 | 12/2004 | Sato et al. | |
| 2005/0025825 A1 | 2/2005 | Heasley et al. | |
| 2005/0031691 A1 | 2/2005 | McGurk et al. | |
| 2005/0152976 A1 | 7/2005 | Chenevier et al. | |
| 2006/0039953 A1 * | 2/2006 | Leung et al. | 424/435 |
| 2007/0275053 A1 | 11/2007 | Lenk | |

FOREIGN PATENT DOCUMENTS

| | | |
|---|---|---|
| CA | 2538755 A1 | 3/2005 |
| EP | 0873749 | 10/1998 |
| EP | 1103253 A2 * | 11/2000 |
| JP | 06218028 | 8/1994 |
| JP | 10231241 | 9/1998 |
| WO | WO-01/76634 A | 10/2001 |

OTHER PUBLICATIONS

International Search Report PCT/US2007/068012.
Database CAPLUS on STN, AN 1996:565491. Jones, R. et al. "Kapanol capsules: Peller formulation provides alternative methods of administration of sustained-release morphine sulfate". Clinical Drug Investigation. 1996, vol. 12, No. 2, pp. 88-93, whole Abstract.

* cited by examiner

*Primary Examiner* — Fereydoun G Sajjadi
*Assistant Examiner* — Ali Soroush
(74) *Attorney, Agent, or Firm* — Alan G. Towner, Esq.; Pietragallo Gordon Alfano Bosick & Rapanti, LLP

(57) ABSTRACT

A flavored, lubricating solution is applied to a solid medicament by spray, dipping, or otherwise coating the medicament. This liquid coating masks the often objectionable taste of the medicament while lubricating it, and thus significantly improving the ability to swallow the medicament. The improvement to the swallowing process is dramatically enhanced with significant reduction in gag reflex, general un-palatability and inability to move the dosage form completely through the mouth, palate, and esophagus to the stomach without sticking or lodging at any point in the process. The solution is a mixture of viscosity-adhesion-lubricity ingredients which includes polyols and polysaccharides, preservative agents, flavoring agents (to improve the palatability of the solution) and optional dispensing agents.

17 Claims, No Drawings

SOLID MEDICAMENT DOSAGE FORM CONSUMPTION AID

CROSS-REFERENCE TO PRIOR APPLICATIONS

Not Applicable

U.S. GOVERNMENT SUPPORT

Not Applicable

BACKGROUND OF THE INVENTION

1. Area of the Art

The present invention is in the area of oral medicaments and more specifically an aid to facilitate the swallowing of solid medicaments.

2. Description of the Background Art

Overview of need: The inability to move a dosage of medication completely through the mouth, palate and down esophagus to the stomach is a significant problem for most children, a large percentage of geriatric patients and a surprisingly high percentage of the general population. This is also a problem with ingestion of products for veterinary care. Obviously, if a patient is unable to swallow medicine or finds swallowing to be very uncomfortable, there is a significant likelihood that patient will "forget" to take the medicine with often serious medical consequences.

There are both a physiological and a psychological aspects to the problem. Although the process of swallowing is actually quite complex involving coordinated peristalsis of the muscles of the esophagus, the process is almost entirely automatic. However, various neurological deficits can make proper swallowing difficult. In such cases the patient may benefit from something that eases the swallowing process. Difficulty in swallowing may result in an uncomfortable feeling that something is stuck in the throat or chest. This may also involve an inability or difficulty in breathing and a resulting choking or gagging reflex. Certainly, there is almost nothing more frightening than an inability to breathe. As a result people who have had any difficulties in swallowing may develop such fear or anxiety that the natural swallowing process is compromised. Thus, a fear of swallowing difficulties may provoke actual swallowing difficulties. A treatment that eases swallowing will benefit such individuals in at least two ways. First, they will actually be able to swallow needed medicaments. Second, after repeated instances of successful swallowing, their anxiety about swallowing will abate and they will continue to enjoy improved swallowing ability.

Physicians often provide a number of tips concerning swallowing including chewing one's food thoroughly and ingesting foods that are largely liquid. This advice, however, does little to help with swallowing solid medicaments. One can hardly chew a pill thoroughly, and although a pill can be powdered, this may alter the proper uptake of the drug and will often result in a truly foul tasting mixture—something that causes a patient to be even less likely to take medications as prescribed. In many cases drugs can be compounded in a liquid form, but with a significant number of pharmaceuticals a liquid dosage is either not possible or at least not practical. Although pharmacists can make up a liquid form of many solid drugs, in a number of cases the liquid dosages are significantly less stable than the solid drug. Often the patient is required to refrigerate the liquid drug solution, and even then full stability and activity is not assured.

This problem is known in the art and a number of attempts have been made to solve it. One popular approach has been to develop coatings for pills and other solid medicaments that facilitate swallowing. For example, U.S. Pat. No. 4,863,741 to Becker describes an enteric coating that facilitates swallowing. U.S. Patent Application No. 2005/0025825 to Heasley et al. describes another coating intended to improve swallowing. Another approach used in the art has been to modify the tried and true method of taking a drink of water to help with swallowing. There are a number of disclosures which modify the viscosity of the liquid used to aid in swallowing. See for example, U.S. Pat. No. 6,277,395 to Fukui et al. which discloses a somewhat viscous drink that apparently helps hold the esophagus open during the swallowing process. However, it does not appear that the art has used a thin liquid coating containing viscosity-adhesion-lubricity agents as opposed to a modified liquid that fills the esophagus around the medicament.

SUMMARY OF THE INVENTION

A flavored, lubricating solution is applied to the solid dosage by spray, dipping, or otherwise coating the medicament. This liquid coating masks the often objectionable taste of the medicament while lubricating the dosage and thus significantly improving the ability to swallow the medicament. The improvement to the swallowing process is dramatically enhanced with significant reduction in gag reflex, general un-palatability and inability to move the dosage form completely through the mouth, palate, and esophagus to the stomach without sticking or lodging at any point in the process. This liquid lubricant can also aid in placement of tubes through the oral and nasal cavities commonly referred to as NG tubes, gastric tubes and other similar devices used in medical practice.

The solution is a mixture of viscosity-adhesion-lubricity ingredients which includes polyols and polysaccharides, preservative agents, flavoring agents (to improve the palatability of the solution) and optional dispensing agents. The viscosity-adhesion-lubricity agents play a central role by adhering to and coating the solid medicament. At the same time these materials are slippery so that the coated medicament can slide down the patient's throat without causing discomfort or gagging. The pleasant sensation of using the solution is further enhanced by the flavoring agents which are generally sweet and mask any unpleasant taste from the medicament. The dispensing agents may be added to reduce foaming or other characteristics which might interfere with application of the solution. The preservative agents are included to prevent any inadvertent microbiological contamination of the solution.

DETAILED DESCRIPTION OF THE INVENTION

The following description is provided to enable any person skilled in the art to make and use the invention and sets forth the best modes contemplated by the inventor of carrying out his invention. Various modifications, however, will remain readily apparent to those skilled in the art, since the general principles of the present invention have been defined herein specifically to provide a liquid to be applied to a solid medicament to improve swallowing of the medicament Ingredients: The inventive swallowing aid is a water-based liquid made with purified water. Generally speaking the mixture contains viscosity-adhesion-lubricity (VAL) modifying agents, flavoring agents, dispensing agents and preservative agents. The VAL agents cause the liquid mixture to coat and adhere to the solid medicament. The VAL agents may also provide a lubricating properties. The flavoring agents are provided to mask unpleasant tastes of medicaments and include sweetening agents. The dispensing agents further modify the physical characteristics of the mixture and make it easier to dispense (e.g., preventing foam formation) and may also contribute to medicament coating as in the case of an added surfactant. The preservative agents prevent microbial growth should the mixture become contaminated.

The VAL ingredients are quite important to the end product. One aspect of the product is adding slipperiness or lubricity to the medicament so it readily passes down the throat. For the lubricity to be effective, the product must evenly coat and adhere to the medicament. Often the surface of a pill is so smooth that an otherwise effective mixture bead up and leave areas of the pill uncoated. This may contribute to sticking of the pill with resulting gagging and general unpleasantness. Surfactants and VAL ingredients improve adhesion-adherence and even coating properties of the product. Increasing the viscosity may also help because a thicker liquid is less likely to bead up. However, the product must not be so viscous as to be sticky and thereby actually impede swallowing.

It should be appreciated that some ingredients may serve more than one function. For example, a sugar alcohol such a sorbitol can be used to modify viscosity and provide lubricity, but since this material is also somewhat sweet in taste, it also acts as a flavoring agent. VAL agents include mostly hydrophilic molecules such as sorbitol (including other sugar alcohols such as galactitol, erythritol, inositol, maltitol, mannitol, ribitol, and xylitol) glycerin, other polyols such as propylene glycol and polyethylene glycol, and polysaccharides such as xanthan gum, carboxymethylcellulose, alginate and carregenan. Other plant gums and cellulose ethers may also be used. Microcrystalline cellulose is a somewhat usual material that can enhance the VAL agents. Microcrystalline cellulose is not soluble per se and contributes opacity to the formula (if so desired). It also contributes viscosity and adhesion of the formula.

Materials like citric acid and sodium citrate generally contribute to the product characteristics and can be considered a flavoring agent (adding tartness). Simethacone, an antifoaming agent, is a useful dispensing agent. Preservative agents include citric acid/sodium citrate, sulfites, propionic acid, methylparaben, propylparaben, benzoates and sorbates, EDTA (ethylene-diamine-tetraacetic acid) and other food grade preservatives known to those of ordinary skill in the art of food science. Many additional preservatives are known to those of ordinary skill in food sciences. Flavoring agents include the usual essential oils and usual fruit flavors. Flavoring agents also include artificial sweeteners such as aspartame, acesulfame, sucralose, and neotame. A preferred formulation is made with FDA approved ingredients and is alcohol free and sugar free.

The actual final formulation will depend on how the product is to be dispensed (i.e., applied to the medicament). Application methods include pouring, dipping, brushing and spraying. I have found that spraying appears to be the most successful application method. Dipping and brushing have the drawback of transferring bits of the medicament into the product container. In addition, microorganisms are readily transferred into the container. Although the preservative agents are included to prevent growth of microorganisms, it is sensible to avoid contamination as much as possible. Pouring wastes product and often fails to evenly coat the medicament. Therefore, a preferred method of application is to place the product in a small pump sprayer such as those sold for applying cleaning fluid to glasses. Formulations intended for spray application need to have a low enough viscosity to permit ready spraying. Methods of application such as pouring can use considerably more viscous formulations.

I have found that a good formula for spray application consists of an aqueous solution of a sugar alcohol and low molecular weight polyol such as glycerin together with a small quantity of preservative and flavoring agent. Both the glycerol and sugar alcohol act as VAL agents and also act as sweeteners. A 50% solution of glycerin has a viscosity around 6 centipoises. A 45% solution of sorbitol has a viscosity of about 170 centipoises so it can be seen that sugar alcohols generally contribute more to the viscosity. A workable formula consists of about 30% to 80% by weight VAL with the remaining weight being water. A usable VAL composition comprises sorbitol between about 0% and 40% and glycerin between about 25% and about 75%. Decreasing the amount of sorbitol reduces the viscosity and somewhat decreases adhesion and coating while at the same time decreasing the overall sweetness of the product (lack of sweetness, however, can be corrected with artificial sweeteners). However, because sorbitol is more expensive than glycerin, manufacturing cost also decrease. The final mixture also contains a small amount (usually less than 1% by weight) of flavoring agent and preservative agent.

A preferred method of using this formulation is to spray the pill or other medicament prior to insertion in the mouth. The pill can be sprayed in a small cup (or similar container) and then picked up and placed into the mouth. Alternatively, the pill can be placed on the palm of the hand and sprayed; however, some users object to having the slippery product on their hands. In most cases liquid like water is used to help swallow the coated medicament. The hydrophilic formula has sufficient viscosity and adhering properties to not be washed off the medicament when the medicament is swallowed with water. In some cases the product works so well that patients have little difficulty in swallowing the medicament without a glass of water.

Product testing results: The product was given to more than thirty healthy and swallowing compromised test subjects from the ages of 4 to 90 years. All were instructed on application by spray and consumption. All test subjects reported significant improvement to the palatability of the medicaments they were consuming and most importantly reported dramatic improvement to the successful ingestion without complication due to the improved lubricity and pre-wetting of the medicament with the adhering solution. The most dramatic improvement was obvious not with the segment of the test subjects who essentially had no significant difficulty with ingestion but rather those individuals that normally displayed an inability to ingest solid medicaments. These subjects represented about 10% of the test population. The most gratifying outcome of the test was that these individuals experienced such dramatic improvements to the quality of life in this respect that they have insisted on continued use of the product after the tests were completed. Several subjects reported the ability to swallow tablets and capsules in large numbers even without water. It is anticipated that the formula will work well for veterinary medicaments (albeit with, perhaps, a different flavoring agent), and veterinary tests are ongoing.

The following claims are thus to be understood to include what is specifically illustrated and described above, what is conceptually equivalent, what can be obviously substituted and also what essentially incorporates the essential idea of the invention. Those skilled in the art will appreciate that various adaptations and modifications of the just-described preferred embodiment can be configured without departing from the scope of the invention. The illustrated embodiment has been set forth only for the purposes of example and that should not be taken as limiting the invention. Therefore, it is to be understood that, within the scope of the appended claims, the invention may be practiced other than as specifically described herein.

I claim:

1. A method for facilitating the swallowing of a solid medicament comprising the steps of:
   providing a sprayer containing a liquid aqueous solution of a viscosity-adhesion-lubricity agent having sufficient viscosity to coat a solid medicament but not so much viscosity as to be sticky, wherein the liquid aqueous solution comprises from 20 to 70 weight percent water;
   operating the sprayer to coat a solid medicament with the liquid aqueous solution; and
   ingesting the coated medicament in pre-wet form with the liquid aqueous solution thereon whereby swallowing the medicament is facilitated.

2. The method according to claim 1, wherein the aqueous solution further comprises an artificial sweetener.

3. The method according to claim 1, wherein the aqueous solution further comprises a preservative agent.

4. The method according to claim 3, wherein the preservative agent is selected from the group consisting of citric acid, sodium citrate, sulfites, propionic acid, methylparaben, propylparaben, benzoates, sorbates, and EDTA.

5. The method according to claim 1, wherein the aqueous solution further comprises a flavoring agent.

6. The method according to claim 1, wherein the viscosity-adhesion-lubricity agent comprises a sugar alcohol selected from the group consisting of galactitol, erythritol, inositol, maltitol, mannitol, ribitol, sorbitol and xylitol.

7. The method according to claim 1, wherein the viscosity-adhesion-lubricity agent comprises a polyol selected from the group consisting of glycerin, propylene glycol and polyethylene glycol.

8. The method according to claim 1, wherein the viscosity-adhesion-lubricity agent comprises a polysaccharide selected from the group consisting of xanthan gum, carboxymethylcellulose, alginate and carregenan.

9. A method of coating a solid medicament to facilitate swallowing thereof comprising applying a liquid formula to the medicament, wherein the liquid formula comprises:
   a viscosity-adhesion-lubricity agent selected from the group consisting of sugar alcohols, polyols, polysaccharides and mixtures thereof;
   flavoring agents; and
   purified water comprising from 20 to 70 weight percent of the liquid formula, whereby the liquid formula has sufficient viscosity to coat a solid medicament but not so much viscosity as to be sticky, wherein the medicament is swallowed in pre-wet form.

10. The method of claim 9, wherein the liquid formula is applied to the solid medicament by spraying.

11. The method of claim 9, wherein the liquid formula further comprises a preservative agent.

12. The method of claim 11, wherein the preservative agent is selected from the group consisting of citric acid, sodium citrate, sulfites, propionic acid, methylparaben, propylparaben, benzoates, sorbates, and EDTA.

13. The method of claim 9, wherein the flavoring agents comprise a sugar alcohol.

14. The method of claim 9, wherein the sugar alcohols are selected from the group consisting of galactitol, erythritol, inositol, maltitol, mannitol, ribitol, sorbitol and xylitol.

15. The method of claim 9, wherein the polyols are selected from the group consisting of glycerin, propylene glycol and polyethylene glycol.

16. The method of claim 9, wherein the polysaccharides are selected from the group consisting of xanthan gum, carboxymethylcellulose, alginate and carregenan.

17. The method of claim 16, wherein the polysaccharides further comprise microcrystalline cellulose.

* * * * *